United States Patent [19]

Holtkamp

[11] Plant 5,016

[45] Mar. 29, 1983

[54] AFRICAN VIOLET PLANT

[76] Inventor: Reinhold Holtkamp, Werther Strasse 112, 4294 Isselburg, Fed. Rep. of Germany

[21] Appl. No.: 305,221

[22] Filed: Sep. 24, 1981

[51] Int. Cl.[3] ..... A01H 5/00
[52] U.S. Cl. ..... Plt./69
[58] Field of Search ..... Plt./69

*Primary Examiner*—James R. Feyrer

*Attorney, Agent, or Firm*—Schwartz, Jeffery, Schwaab, Mack, Blumenthal & Koch

[57] ABSTRACT

A new African violet cultivar named Pink Delaware which is a sport of Delaware, disclosed in U.S. Plant Pat. No. 4,213. Pink Delaware is characterized by its pink flower color and relatively large flower size, its upright and strong flower stems which rigidly support the large flowers to provide a relatively tight and profuse corolla; compact growth habit; and by its continuous and uniform flowering, with flowers appearing approximately 6–8 weeks after potting.

1 Drawing Figure

The present invention comprises a new and distinct cultivar of African violet plant, botanically known as *Saintpaulia ionantha,* and hereinafter referred to by the cultivar name Pink Delaware.

The new cultivar was referred to during the selection process by the designation 52 M, and the cultivar is a sport of Delaware, disclosed in my U.S. Plant Pat. No. 4,213, granted Feb. 14, 1978. Pink Delaware is similar in all essential respects to Delaware except for its pink flower color.

The new cultivar Pink Delaware was discovered in a flowering block of the parent cultivar Delaware, and subsequently selected. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Pink Delaware has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Pink Delaware, which in combination distinguish this African violet as a new and distinct cultivar:

1. Relatively large, star-shaped flowers which are pink in color.
2. Very upright and strong flower stems which rigidly support the large flowers to provide a tight, profuse corolla.
3. Compact plant habit.
4. Continuous flowering.
5. Flowers very uniformly, with the first flowers appearing approximately 6–8 weeks after potting.
6. Long-lasting and non-dropping blossoms.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical Classification: *Saintpaulia ionantha,* Ramat. cv. Pink Delaware.

Parentage: Sport of Delaware, disclosed in U.S. Plant Pat. No. 4,213.

Plant: From 7 cm. to 9 cm. tall when grown in pots, and approximately 22–25 cm. in diameter when fully grown.

Leaves:

*General form.*—Heart-shaped.

*Diameter.*—55 mm.

*Texture.*—Soft and slightly hairy.

*Aspect.*—Velvety, slightly shiny.

*Veins.*—Upperside visible, underside well-pronounced, shiny, light green with brown tint on older leaves and darker on younger leaves.

*Color (upperside).*—HCC spinach green 0960.

*Color (underside).*—HCC sage green 000861/3 with purple tint.

*Petiole.*—Young petiole greenish brown, hairy; old petiole brownish green.

Flowers:

*Buds.*—Bell-shaped; 10 mm. just before opening; 5–7 per stem.

*Sepals.*—Color: Brownish green. Calyx: Funneled. Aspect: Spear-shaped. Peduncle: Normal, strong, upright.

Individual flowers:

*Size.*—35–45 mm.

*Color.*—Upperside: Between magnolia purple 030/2-1, center a tone deeper. Underside: Magnolia purple 030/3.

*Borne.*—Flower stem carries 5–7 flowers on normal strong peduncles; flowers occasionally display an additional small petal in center of bloom.

*Shape.*—Star-shaped, wavy; 5–7 petals, same size.

*Flowering time.*—First flowers appear 6–7 weeks after potting; after 8–9 weeks full flowering saleable plant.

Reproductive organs:

*Stamens.*—5–7 anthers, composed of 2 cells, with seed capsule slightly pushed through.

*Anthers.*—HCC Dresden yellow 64.

*Filaments.*—3 mm. long; yellowish green.

*Styles.*—7 mm. light pink with white stigma;

*Pollen color.*—HCC Dresden yellow 64/3.

Roots: White when young and active; greenish brown when older; normally developed.

Disease resistance: Good as experienced to date.

I claim:

1. A new and distinct cultivar of African violet plant known by the cultivar name Pink Delaware and particularly characterized by the combined features of pink flower color, very upright and strong flower stems which rigidly support relatively large flowers in a tight and profuse corolla; continuous flowering, compact growth habit, very uniform flowering and vigorous growth, with flowers appearing 6–7 weeks after potting, and a full flowering plant after 8–9 weeks.

* * * * *

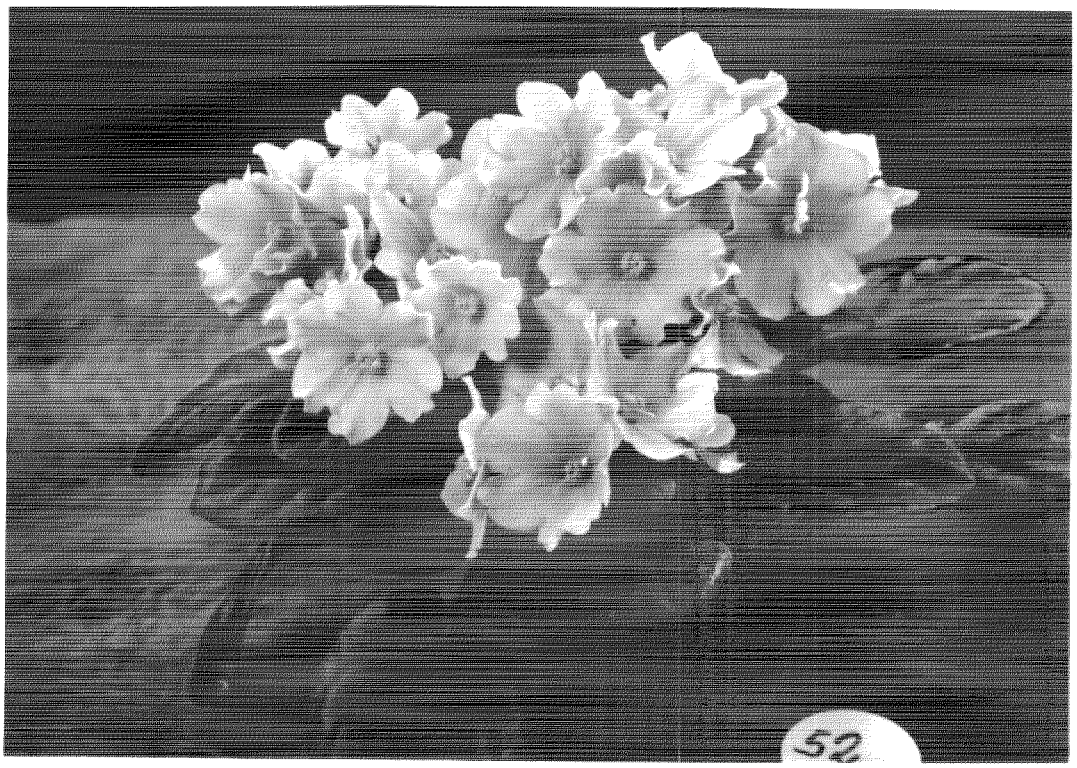
52